United States Patent
Hansel et al.

(10) Patent No.: US 9,969,845 B2
(45) Date of Patent: May 15, 2018

(54) HYDROXYL-CONTAINING POLY(ALKYLENE PHOSPHATES)

(71) Applicant: LANXESS Deutschland GmbH, Cologne (DE)

(72) Inventors: Jan-Gerd Hansel, Bergisch Gladbach (DE); Heiko Tebbe, Dormagen (DE); Michael Wittpahl, Nettetal (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days. days.

(21) Appl. No.: 14/989,176

(22) Filed: Jan. 6, 2016

(65) Prior Publication Data

US 2016/0215101 A1 Jul. 28, 2016

(30) Foreign Application Priority Data

Jan. 27, 2015 (EP) .................................. 15152591

(51) Int. Cl.
| | |
|---|---|
| C08G 18/48 | (2006.01) |
| C08G 79/04 | (2006.01) |
| C09K 21/12 | (2006.01) |
| C07F 9/09 | (2006.01) |
| C08K 5/521 | (2006.01) |
| C08G 18/66 | (2006.01) |
| C08G 18/76 | (2006.01) |
| C08G 18/16 | (2006.01) |
| C08G 18/18 | (2006.01) |
| C08G 18/24 | (2006.01) |
| C08G 18/38 | (2006.01) |
| C08G 101/00 | (2006.01) |

(52) U.S. Cl.
CPC .............. *C08G 79/04* (2013.01); *C07F 9/093* (2013.01); *C08G 18/165* (2013.01); *C08G 18/1833* (2013.01); *C08G 18/244* (2013.01); *C08G 18/3885* (2013.01); *C08G 18/4825* (2013.01); *C08G 18/6666* (2013.01); *C08G 18/7621* (2013.01); *C08K 5/521* (2013.01); *C09K 21/12* (2013.01); *C08G 2101/0008* (2013.01); *C08G 2101/0083* (2013.01)

(58) Field of Classification Search
CPC ... C07F 9/093; C08G 18/165; C08G 18/1833; C08G 18/244; C08G 18/3885; C08G 18/4825; C08G 18/6666; C08G 18/7621; C08G 79/04; C08G 2101/0008; C08G 2101/0083; C08K 5/0066; C08K 5/521; C08L 75/04; C08L 75/08; C09K 21/00; C09K 21/12

See application file for complete search history.

(56) References Cited

U.S. PATENT DOCUMENTS

| | | | |
|---|---|---|---|
| 3,580,890 A | 5/1971 | Diehr et al. | |
| 3,620,896 A | 11/1971 | Diehr et al. | |
| 3,629,545 A | 12/1971 | Wilcox | |
| 3,764,640 A | 10/1973 | Klose | |
| 3,767,732 A | 10/1973 | Klose | |
| 3,891,727 A | 6/1975 | Weil | |
| 3,959,414 A | 5/1976 | Shim et al. | |
| 3,959,415 A | 5/1976 | Shim et al. | |
| 4,012,463 A | 3/1977 | Walsh et al. | |
| 4,248,930 A | 2/1981 | Haas et al. | |
| 4,263,408 A | 4/1981 | Meyborg et al. | |
| 4,458,035 A * | 7/1984 | Hardy ..................... | C07F 9/093 521/107 |
| 5,238,982 A * | 8/1993 | Adhya ................... | C08K 5/521 264/178 F |
| 5,608,100 A | 3/1997 | Sicken | |
| 5,728,746 A | 3/1998 | Sicken | |
| 5,985,965 A | 11/1999 | Sicken et al. | |
| 9,315,677 B2 * | 4/2016 | Fujita ....................... | C09D 5/18 |
| 2005/0159500 A1 | 7/2005 | Dreier et al. | |
| 2014/0024734 A1 | 1/2014 | Hansel et al. | |

FOREIGN PATENT DOCUMENTS

| | | |
|---|---|---|
| EP | 0448159 A1 | 9/1991 |
| GB | 1211405 | 11/1970 |

OTHER PUBLICATIONS

Adam, Norbert et al., "Polyurethanes", Ullmann's Encyclopedia of Industrial Chemistry, 7th ed., chap 7 ("Foams"), Wiley-VCH, Weinheim 2005, pp. 542-587.

Kunstoff-Handbuch, vol. VII, Carl Hanser Verlag, Munich, 1993, pp. 104-123.

Bliznyuk, N.K., et al. "Bis (.beta.-hydroxyethoxyphosphoryl) ethylene glycol", Database CA [Online] chemical Abstracts Service, Columbus, Ohio, US, Database accession No. 1976:16748.

Vives, Jean Pierre et al., "some cyclic phosphoric esters. I. Preparation and hydrolysis", Database CA [Online] chemical Abstracts Service, Columbus, Ohio, US, Database accession No. 1965:480110.

European Search Report from European Application No. 15152591, dated Jul. 20, 2015, 4 pages.

Weil, Edward D., et al., "Oligomeric Phosphorus Esters with Flame Retardant Utility", J. Fire Retardant Chem, 1982, 9, pp. 39-49.

* cited by examiner

*Primary Examiner* — John Cooney

(57) ABSTRACT

Flame retardant compositions for polyurethanes may include hydroxyl-containing poly(alkylene phosphates) that have 5 mol % or less of phosphorus from phosphorus-containing compounds having a $^{31}$P NMR resonance signal at a chemical shift in the range from 13 ppm to 18 ppm relative to 85 wt % phosphoric acid.

12 Claims, No Drawings

HYDROXYL-CONTAINING POLY(ALKYLENE PHOSPHATES)

The present invention relates to compositions comprising hydroxyl-containing poly(alkylene phosphates), to a process for the production thereof and to the use thereof as flame retardants in polyurethanes.

BACKGROUND INFORMATION

Polyurethanes are employed in many application fields, such as furniture, mattresses, transport, electrical, construction and industrial insulation. To achieve the high flame retardancy requirements demanded of materials for, inter alia, automotive, railway and aeroplane interiors and also for buildings insulation, polyurethanes and in particular polyurethane foams generally require treatment with flame retardants. To this end, a great many different flame retardants are already known and commercially available. However, there are often appreciable technical issues and/or toxicological concerns surrounding their use.

When, for instance, solid flame retardants are used, for example melamine, ammonium polyphosphate or ammonium sulphate, sedimentation or aggregation gives rise to metering problems which often necessitate technical modifications to the foaming equipment, i.e. costly and inconvenient revamping and rejigging.

It is true that the commonly used chloroalkyl phosphates tris(chloroethyl) phosphate, tris(chloroisopropyl) phosphate and tris(dichloroisopropyl) phosphate are readily meterable liquids. However, a recent but increasingly common requirement of open-cell flexible polyurethane foam systems for automotive interiors is that the gaseous emissions (volatile organic compounds, VOCs) and especially the condensable emissions (fogging) from these foams shall not exceed low limits. The liquids referred to above no longer meet these requirements owing to their excessive volatility.

Fogging refers to the undesired condensation of evaporated volatile constituents from the motor vehicle interior on glass panes, in particular on the windscreen. This phenomenon is quantifiable according to DIN 75 201 B. The automotive industry typically requires that the fogging condensate as determined by the DIN 75201 B method shall be less than 1 mg.

Furthermore, halogen-free flame retardants are preferred from ecotoxicological aspects and also by reason of ameliorated fire side-effects regarding smoke gas density and smoke gas toxicity. Halogen-free flame retardants may also be of particular interest for performance reasons. For instance, severe corrosion is observed on the plant components used for flame lamination of polyurethane foams when halogenated flame retardants are used. This is attributable to the emissions of hydrohalic acid which arise during the flame lamination of halogen-containing polyurethane foams.

Flame lamination refers to a process for bonding textiles and foams together wherein one side of a foam sheet is incipiently melted by means of a flame and immediately thereafter pressed together with a textile web.

The halogen-free liquid flame retardant systems hitherto disclosed, for example triethyl phosphate or other alkyl or aryl phosphates, such as diphenyl cresyl phosphate for example, provide only inadequate compliance with the abovementioned requirements for low levels of VOCs or low levels of fogging, or exhibit inadequate flame retardancy.

Hydroxyl-containing poly(alkylene phosphates) provide solutions in the sense of low fogging contributions. These substances contain alcoholic hydroxyl groups which during production of the polyurethane foams react with the polyisocyanates employed and thus ensure that the flame retardants are securely embedded in the polymer matrix. Hydroxyl-containing poly(alkylene phosphates) and processes for the production thereof are prior art, for example from DE-A 20 36 587, DE-A 20 36 595 B1, EP-A 0 658 561, EP-A 0 658 580 or EP-A 0 771 810.

The hydroxyl-containing poly(alkylene phosphates) described in the cited prior art have disadvantages. Their production requires the use of the phosphorus-containing raw material phosphorus pentoxide. Phosphorus pentoxide is a highly corrosive, extremely hygroscopic solid which is difficult and dangerous to handle. A synthesis of hydroxyl-containing poly(alkylene phosphates) using raw materials that are easier to handle is therefore desirable.

In addition, the prior art production processes afford the hydroxyl-containing poly(alkylene phosphates) in impure form. The production of said poly(alkylene phosphates) forms undesired phosphorus-containing compounds, in particular five-membered, cyclic phosphates. E. D. Well, R. B. Fearing, F. Jaffe, *J. Fire Retardant Chem.*, 1982, 9, 39 reports that the presence of these five-membered, cyclic phosphates may be readily detected by $^{31}$P NMR spectroscopy since their resonance signal appears at a chemical shift of 17-18 ppm and thus stands out clearly from the signals of the main products (poly(alkylene phosphates)). According to Weil et al. the presence of these five-membered, cyclic phosphates results in undesired susceptibility to hydrolysis and in acid formation. Furthermore, poly(alkylene phosphates) having a high content of such undesired phosphorus-containing compounds, in particular of five-membered, cyclic phosphates, also contain more volatile components and thus also lead to elevated amounts of fogging condensate.

The problem of the occurrence of undesired phosphorus-containing by-products, in particular five-membered, cyclic phosphates, during production of phosphorus-containing oligomeric condensation products has been known about for a long time and there have been numerous proposals for solving it as is evidenced by U.S. Pat. No. 3,891,727, U.S. Pat. No. 3,959,415, U.S. Pat. No. 3,959,414, U.S. Pat. No. 4,012,463 and EP-A 0 448 159. In all of these proposed solutions the avoidance or reduction in the levels of such impurities involves increased cost and complexity, for example in the form of downstream purification steps, in the synthesis of these phosphorus-containing oligomeric condensation products.

An improved route to hydroxyl-containing poly(alkylene phosphates) having a relatively low content of undesired phosphorous-containing by-products, in particular five membered, cyclic phosphates, is therefore desirable. The present invention has for its object the provision of hydroxyl-containing poly(alkylene phosphates) which overcome the cited disadvantages of the prior art.

SUMMARY

It has been found that a new production process makes it possible to produce compositions comprising hydroxyl-containing poly(alkylene phosphates) which, surprisingly, have a low content of undesired phosphorus-containing compounds.

The present invention accordingly provides a composition comprising
at least one hydroxyl-containing poly(alkylene phosphate) of formula (I)

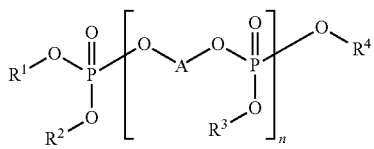

(I)

where
n is an integer from 1 to 100,
$R^1$, $R^2$, $R^3$ and $R^4$ independently of one another represent a $C_1$- to $C_8$-alkyl radical or a radical of formula $-(CHR^5-CHR^6-O)_m-H$,
where
m is an integer from 1 to 5 and
$R^5$ and $R^6$ independently of one another represent hydrogen or methyl,
with the proviso that one or more of the radicals but not simultaneously all of the radicals $R^1$, $R^2$, $R^2$ and $R^4$ represent a radical of formula $-(CHR^5-CHR^6-O)_m-H$,
A represents a straight-chain or branched $C_4$- to $C_{20}$-alkylene radical or a $C_3$- to $C_6$-cycloalkylene radical, or
A represents a radical of formula $-CH_2-CH=CH-CH_2-$, a radical of formula $-CH_2-C\equiv C-CH_2-$, a radical of formula $-CHR^5-CHR^6-(O-CHR^7-CHR^8)_a-$, a radical of formula $-CHR^5-CHR^6-S(O)_b-CHR^7-CHR^8-$ or a radical of formula $-(CHR^5-CHR^6-O)_c-R^9-(O-CHR^7-CHR^8)_d-$,
where
a is an integer from 0 to 5,
b is an integer from 0 to 2,
c and d are, independently of one another, an integer of 1 to 5,
$R^5$, $R^6$, $R^7$ and $R^8$ independently of one another represent hydrogen or methyl,
$R^9$ represents the radical $-CH_2-CH=CH-CH_2-$, the radical $-CH_2-C\equiv C-CH_2-$, a 1,2-phenylene radical, a 1,3-phenylene radical, a 1,4-phenylene radical, or a radical of formula (II)

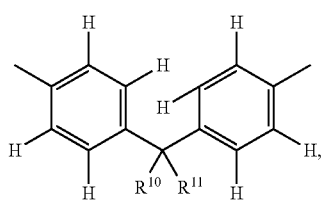

(II)

or a radical of formula (III)

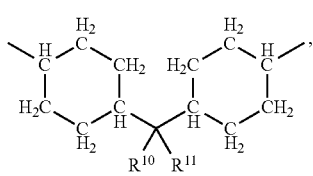

(III)

or a radical of formula (IV)

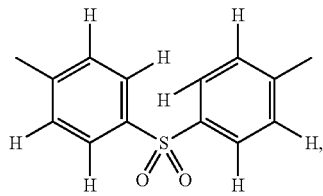

(IV)

or a radical of formula $-C(=O)-R^{12}-C(=O)-$,
wherein
$R^{10}$ and $R^{11}$ each independently of one another represent hydrogen or $C_1$- to $C_4$-alkyl,
or $R^{10}$ and $R^{11}$ together with the carbon atom to which they are bonded represent an optionally alkyl-substituted carbocyclic ring having 4 to 8 carbon atoms,
and
$R^{12}$ represents a straight-chain or branched $C_2$- to $C_8$-alkylene radical, a $C_3$- to $C_6$-cycloalkylene radical, a 1,2-phenylene radical, a 1,3-phenylene radical, or a 1,4-phenylene radical,
wherein, in the $^{31}P$ NMR spectrum of the composition acquired in $CDCl_3$ as solvent with 85 wt % phosphoric acid as external standard, the area under all resonance signals from 13 to 18 ppm amounts to 5 percent or less of the total area of all resonance signals from −30 to 200 ppm.

In formula (I) one or more of the radicals $R^1$, $R^2$, $R^3$ and $R^4$ represent $-(CHR^5-CHR^6-O)_m-H$ but not simultaneously all of the radicals $R^1$, $R^2$, $R^3$ and $R^4$ represent $-(CHR^5-CHR^6-O)_m-H$, by contrast one or more of the radicals $R^1$, $R^2$, $R^3$ and $R^4$ represent $C_1$- bis $C_8$-alkyl.

In a preferred embodiment of the invention, in formula (I) one of the radicals $R^1$, $R^2$, $R^3$ and $R^4$ represents $-(CHR^5-CHR^6-O)_m-H$ and three of the radicals $R^1$, $R^2$, $R^3$ and $R^4$ represent $C_1$- to $C_8$-alkyl.

In a likewise preferred embodiment of the invention, in formula (I) two of the radicals $R^1$, $R^2$, $R^3$ and $R^4$ represent $-(CHR^5-CHR^6-O)_m-H$ and two of the radicals $R^1$, $R^2$, $R^3$ and $R^4$ represent $C_1$- to $C_8$-alkyl.

In a likewise preferred embodiment of the invention, in formula (I) three of the radicals $R^1$, $R^2$, $R^3$ and $R^4$ represent $-(CHR^5-CHR^6-O)_m-H$ and one of the radicals $R^1$, $R^2$, $R^3$ and $R^4$ represent $C_1$- to $C_8$-alkyl. The $C_1$- to $C_8$-alkyl radicals referred to in the definition of $R^1$, $R^2$, $R^3$ and $R^4$ are preferably identical and represent in particular ethyl, n-propyl, isopropyl, n-butyl or isobutyl.

It is preferable when A represents a straight-chain $C_4$- to $C_6$-alkylene radical.

It is likewise preferable when A represents a radical of formula $-CHR^5-CHR^6-(O-CHR^7-CHR^8)_2-$, where a is a number from 0 to 2 and $R^5$, $R^6$, $R^7$ and $R^8$ are identical and represent hydrogen.

Preference is given to a composition comprising at least one hydroxyl-containing poly(alkylene phosphate) of formula (I)

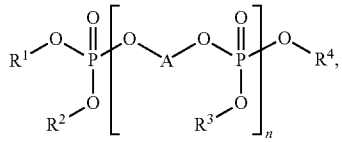

(I)

where
n is an integer from 1 to 10,
$R^1$, $R^2$, $R^3$ and $R^4$ independently of one another represent ethyl, n-propyl, isopropyl, n-butyl or isobutyl or a radical of formula —$(CHR^5$—$CHR^6$—$O)_m$—H,
where
m is an integer from 1 to 2, and
$R^5$ and $R^6$ independently of one another represent hydrogen or methyl,
with the proviso that one or more of the radicals but not simultaneously all of the radicals $R^1$, $R^2$, $R^3$ and $R^4$ represent a radical of formula —$(CHR^5$—$CHR^6$—$O)_m$—H,
A represents a straight-chain $C_4$- to $C_5$-alkylene radical or a radical of formula

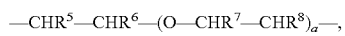

where
a is an integer from 0 to 2
and
$R^5$, $R^6$, $R^7$ and $R^8$ independently of one another represent hydrogen or methyl.

Particular preference is given to a composition comprising at least one hydroxyl-containing poly(alkylene phosphate) of formula (I)

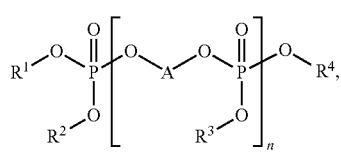

(I)

where
n is an integer from 1 to 10,
$R^1$, $R^2$, $R^3$ and $R^4$ independently of one another represent ethyl, n-propyl or n-butyl or a radical of formula —$(CHR^5$—$CHR^6$—$O)_m$—H,
where
m is 1 or 2 and
$R^5$ and $R^6$ independently of one another represent hydrogen or methyl,
with the proviso that one or more of the radicals but not simultaneously all of the radicals $R^1$, $R^2$, $R^3$ and $R^4$ represent a radical of formula —$(CHR^5$—$CHR^6$—$O)_m$—H,
A represents a straight-chain $C_4$-alkylene radical or a radical of formula

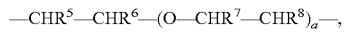

where
a is 0 or 1,
$R^5$ and $R^6$ independently of one another represent hydrogen or methyl,
and
$R^7$ and $R^8$ are identical and represent hydrogen.

Very particular preference is given to compositions according to the invention comprising at least a hydroxyl-containing poly(alkylene phosphate) of formula (I) where the radicals $R^1$, $R^2$, $R^3$ and $R^4$ represent ethyl or the radical —$CH_2$—$CHCH_3$—OH or —$CHCH_3$—$CH_2$—OH, wherein one or more of the radicals but not simultaneously all of the radicals $R^1$, $R^2$, $R^3$ and $R^4$ represent —$CH_2$—$CHCH_3$—OH or —$CHCH_3$—$CH_2$—OH and A represents the radical —$CH_2CH_2OCH_2CH_2$—.

In a preferred embodiment of the invention the composition according to the invention comprises a mixture of distinct hydroxyl-containing poly(alkylene phosphates) of formula (I) which differ from one another at least in the number n of repeating units and/or indices a, b, c, d, m and thus in their molar mass. It is particularly preferable when the composition according to the invention comprises mixtures of such isomeric and/or oligomeric hydroxyl-containing poly(alkylene phosphates) of formula (I). In this case it is possible to characterize the oligomeric mixture by the mean of the cited numbers.

It is preferable when the compositions according to the invention are halogen-free. The term "halogen-free" is to be understood as meaning that the compositions comprise no other substances in an amount sufficient to bring about a content of the elements fluorine, chlorine, bromine and/or iodine of greater than 5000 ppm based on the total composition.

It is preferable when the compositions comprising hydroxyl-containing poly(alkylene phosphates) of formula (I) according to the invention are substances liquid at processing temperature. Here, processing temperature is to be understood as meaning the temperature at which the polyurethane raw materials are fed to the metering and mixing assemblies of the production equipment. In general, temperatures between 20 and 80° C. are chosen here according to the viscosities of the components and the design of the metering assemblies.

The compositions according to the invention preferably have a viscosity between about 10 mPas and about 10,000 mPas at 23° C. The viscosity is the so-called dynamic viscosity determinable, for example, with an "SVM 3000" viscometer from Anton Paar GmbH.

The hydroxyl number of the compositions according to the invention is generally about 15 to about 300, preferably about 30 to about 250 mg KOH/g. The hydroxyl number indicates the amount of potassium hydroxide in milligrams which is equivalent in an acetylation to the acetic acid quantity bound by one gram of substance. The hydroxyl number may be determined in a manner known to those skilled in the art, for example as described in DIN 53240.

The phosphorus content of the compositions according to the invention is generally about 10 to about 20 wt %, preferably about 12 to about 18 wt % based on the total composition.

The phosphorus content may be determined in a manner known to those skilled in the art, for example gravimetrically. To this end, the organic substance, in the present case the composition according to the invention, is initially "digested", i.e. decomposed into generally inorganic fragments, in this case especially into soluble, inorganic phosphate/phosphoric acid, using acid, optionally oxidants and using heat and/or pressure. The phosphate/the phosphoric acid is then precipitated, for example by addition of ammonium heptamolybdate solution as sparingly soluble ammonium molybdophosphate, and determined gravimetrically. However, those skilled in the art are also familiar with alternative methods of quantification after digestion, for example by colourimetry.

In the $^{31}$P NMR spectra of the compositions according to the invention acquired in $CDCl_3$ as solvent with 85 wt % phosphoric acid as external standard, the area under all resonance signals from about 13 to about 18 ppm amounts to about 5 percent or less, preferably about 3 percent or less, of the total area of all resonance signals in the measured range from −30 to 200 ppm.

The thus determined area percent values may be treated as virtually equal to mol percent. It follows that the compositions according to the invention have 5 mol % or less, preferably 3 mol % or less, of phosphorus from phosphorus-containing compounds having a $^{31}$P NMR resonance signal at a chemical shift in the range from 13 ppm to 18 ppm relative to 85 wt % phosphoric acid as external standard, wherein the amount reported in mol % relates to the sum of all phosphorus atoms present in the composition and was determined by quantitative $^{31}$P NMR spectroscopy.

These phosphorus-containing compounds are in particular cyclic five-membered phosphoric esters having at least one structural unit of formula

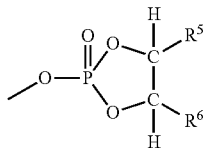

where $R^5$ and $R^6$ independently of one another represent hydrogen or methyl.

In the context of the present invention the area under all resonance signals e from about −30 to about 200 ppm was determined by quantitative $^{31}$P NMR spectroscopy.

The method of $^{31}$P NMR spectroscopy is known to those skilled in the an. To acquire the $^{31}$P NMR spectra in the case of the present invention initially 100 mg of the inventive composition to be analyzed were weighed out with the greatest possible accuracy, dissolved in 5 ml of deuterated chloroform (CDCl$_3$) and transferred into an NMR sample tube of 5 mm in diameter. The present NMR spectroscopic analyses were and are performed using a Bruker DPX-400 instrument. The spectra are acquired at 161.9 MHz with a delay of 1 s, 256 scans+2 dummy scans, a pulse duration of 6.5 μs and a sweep width of 81521.7 Hz. The chemical shift of the resonance signals was reported relative to 85 wt % phosphoric acid as the external standard.

To provide quantitative evaluation the areas under the respective resonance signals were and are manually integrated within the reported limits of −30 to 200 ppm. According to the invention the sum of all areas thus determined was and is normalized to 100% and the area under the resonance signals in the range from 13 to 18 ppm calculated as a percentage.

The present invention further relates to a novel process for preparing the compositions according to the invention.

The present invention provides a process for producing a composition comprising at least one hydroxyl-containing poly(alkylene phosphate) of formula (I)

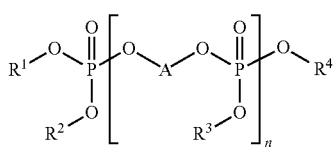

where the substituents $R^1$ to $R^4$ and the index n have the general and preferred meanings previously presented above for formula (I), wherein the process includes
a) reacting a poly(alkylene chlorophosphate) of formula (V),

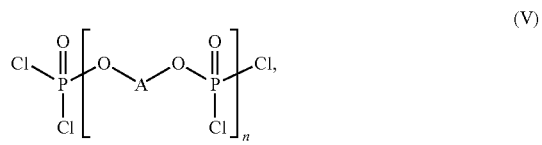

where A and n have the general and preferred meaning indicated above in the definition of formula (I), with a mixture comprising at least one $C_1$- to $C_8$-alcohol and water, and
b) reacting the product of the reaction from a) with at least one compound of formula (VI)

where
X represents —O— or —O—C(=O)—O— and
$R^5$ and $R^6$ have the general and preferred meanings indicated above in the definition of formula (I).

The poly(alkylene chlorophosphates) of formula (V) are preferably produced from phosphorus oxychloride and a diol of formula HO-A-OH where A has the general and preferred meaning indicated above in the definition of formula (I). These substances and processes for the production thereof are disclosed, for example, in EP-A 2 687 534. The inventive production process accordingly proceeds from phosphorus oxychloride which, being a liquid, is substantially easier to handle than the solid phosphorus pentoxide.

It is preferable when the mixture employed in step a) of the process according to the invention comprises at least one $C_1$- to $C_8$-alcohol and 1 mol % to 75 mol % of water based on the sum of $C_1$- to $C_8$-alcohol and water. It is particularly preferable when the mixture comprises 5 mol % to 40 mol % of water based on the sum of $C_1$- to $C_8$-alcohol and water.

The process according to the invention employs the mixture of $C_1$- to $C_8$-alcohol and water in an amount such that the sum of the moles of $C_1$- to $C_8$-alcohol and water is at least equal to the number of moles of chlorine atoms present in the poly(alkylene chlorophosphate) of formula (V). It is preferable to employ an excess of the mixture of $C_1$- to $C_8$-alcohol and water relative to the chlorine atoms present in the poly (alkylene chlorophosphate) of formula (V). It is particularly preferable when the sum of the moles of $C_1$- to $C_8$-alcohol and water is 2 to 10 times the number of moles of the chlorine atoms present in the poly(alkylene chlorophosphate) of formula (V).

Suitable $C_1$- to $C_8$-alcohols are in particular ethanol, n-propanol, isopropanol, n-butanol and/or isobutanol. Particular preference is given to ethanol, n-butanol or mixtures thereof.

The product from step a) is generally isolated or reacted with the compound (VI) without an intermediate isolation. The amount of compound (VI) employed is determined by the amount of water employed in step a). The process generally employs 0.1 to 10 mol of the compound (VI) per 1 mol of water, preferably employs 0.5 to 5 mol of the compound (VI) per 1 mol of water and particularly preferably employs 0.9 to 2.5 mol of the compound (VI) per 1 mol of water.

The compound of formula (VI) employed in step b) of the process according to the invention is preferably an alkylene oxide, for example ethylene oxide, propylene oxide, 1,2-butylene oxide or glycidol, or an alkylene carbonate, for example ethylene carbonate or propylene carbonate. It is particularly preferable when the compound of formula (VI) is ethylene oxide, propylene oxide or a mixture of these two compounds.

Step a) of the process according to the invention is generally carried out at a temperature in the range from −20° C. to +100° C. Step a) of the process according to the invention is preferably carried out at a temperature in the range from −10° C. to +80° C. and particularly preferably at a temperature in the range from 0° C. to +50° C.

Step a) of the process according to the invention is generally carried out at a pressure in the range from 1 mbar to 3000 mbar, preferably from 5 mbar to 2500 mbar and particularly preferably from 10 mbar to 2000 mbar.

The reaction in step a) is generally carried out by contacting the reaction participants with one another continuously or batchwise and maintaining the reaction temperature in the desired range by heating or removing reaction heat. It is preferable when the hydrogen chloride formed in the reaction is removed from the reaction mixture during or after the reaction in a manner known per se, for example by evaporation.

In an alternative, likewise preferred embodiment of the invention the hydrogen chloride is neutralized by a base. This base may be added to the reaction mixture either at the beginning of the reaction or once the reaction is virtually complete. The coproduct formed from base and hydrogen chloride is subsequently removed from the reaction mixture by known methods, for example filtration or aqueous extraction. Bases suitable for the process according to the invention include inorganic bases, for example metal hydroxides, oxides, carbonates, hydrogencarbonates and the like, or organic bases, for example trialkylamines, pyridine, amidine, guanidine and the like.

Any excess of $C_1$- to $C_8$-alcohol and/or water in the reaction mixture may be removed by known methods, preferably by distillation, before carrying out step b).

Step b) of the process according to the invention is generally carried out at a temperature in the range from 0° C. to +180° C. Step b) of the process according to the invention is preferably carried out at a temperature in the range from 10° C. to +160° C. and particularly preferably at a temperature in the range from 20° C. to +140° C.

Step b) of the process according to the invention is generally carried out at a pressure from about 100 mbar to about 6000 mbar, preferably about 500 mbar to about 6000 mbar and particularly preferably about 950 mbar to about 6000 mbar.

The reaction in step b) is generally carried out by heating the intermediate product obtained from step a) to the reaction temperature by supplying heat and subsequently adding the compound of formula (VI) in continuous or portionwise fashion. Once the desired conversion has been achieved any excess of the compound of formula (VI) and any other volatile substances are removed by known methods, preferably by distillation. This may be followed by further purifying operations, for example clarification, decolourization, filtration and the like.

In a preferred embodiment of the invention the composition according to the invention comprises a mixture of different isomeric and/or oligomeric hydroxyl-containing poly(alkylene phosphates) of formula (I). The process according to the invention specified hereinabove may be used to produce an oligomer mixture composed of molecules of different chain length n (characterized by the mean of the chain length n for example) by employing in the process a mixture of at least two different poly(alkylene chlorophosphates) of formula (V) which distinguish themselves from one another in terms of the value of the number n.

The invention further provides for the use of the compositions according to the invention as flame retardants for synthetic and natural materials, for example synthetic polymers, modified or unmodified natural polymers, wood-based materials, leather and paper. Said compositions are particularly suitable for reactive resins, for example polyurethanes and epoxy resins, on account of their reactive nature.

For use as flame retardants the compositions according to the invention may comprise further flame retardants, auxiliary/added substances.

The present invention further provides flame retardant preparations comprising a composition according to the invention and one or more auxiliary/added substances B).

Examples of suitable auxiliary/added substances B) include solvents, for example water or alkyl esters of aliphatic or aromatic di- or tricarboxylic acids, antioxidants and stabilizers, for example sterically hindered trialkyl phenols, alkyl esters of 3-(3,5-di-tert-butyl-4-hydroxyphenyl) propionic acid, benzofuran-2-one, secondary aromatic amines, phosphites, phenothiazine or tocopherols, colourants, for example iron oxide pigments or carbon blacks, and also flame retardants distinct from the poly(alkylene phosphates) of formula (I) according to the invention.

The flame retardant preparations preferably comprise
  about 10 to about 90 wt % of composition according to the invention,
  about 10 to about 90 wt % of at least one auxiliary/added substance B),
wherein the amounts of the components are to be selected within the specified ranges such that the components sum to 100 wt %.

In a preferred embodiment the flame retardant preparation according to the invention comprises as auxiliary/added substance B) at least one flame retardant from the group triethyl phosphate, triphenyl phosphate, diphenyl cresyl phosphate, tricresyl phosphate, isopropylated or butylated aryl phosphates, bisphenol-A bis(diphenyl phosphate), resorcinol bis(diphenyl phosphate), neopentyl glycol bis (diphenyl phosphate), tris(chloroisopropyl) phosphate, tris (dichloropropyl) phosphate, dimethyl methaneospsphonate, diethyl ethanephosphonate, dimethyl propanephosphonate, diethylphosphinic acid derivatives and salts, other oligomeric phosphates or phosphonates, hydroxyl-containing phosphorus compounds, 5,5-dimethyl-1,3,2-dioxaphosphorinane 2-oxide derivatives, 9,10-dihydro-9-oxa-10-phosphhaphenanthrene 10-oxide (DOPO) and derivatives thereof, ammonium phosphate, ammonium polyphosphate, melamine phosphate, melamine polyphosphate, melamine, melamine cyanurate, alkyl esters of a tetrabromobenzoic acid, bromine containing diols produced from tetrabromophthalic anhydride, bromine-containing polyols, bromine-containing diphenyl ethers, aluminium hydroxide, boehmite, magnesium hydroxide, expandable graphite and clay minerals.

The invention further provides a flame retardant polyurethane comprising as the flame retardant an inventive composition or an inventive flame retardant preparation.

The flame retardant polyurethane according to the invention is obtainable by reacting organic polyisocyanates with compounds having at least two isocyanate-reactive hydrogen atoms with customary blowing agents, stabilizers, activators and/or further customary auxiliary/added substances in the presence of a composition according to the invention. The thus produced polyurethane may comprise the composition according to the invention either in its original form or in the form of its derivatives. These derivatives are formed by reaction of the polyurethane raw materials, in particular the polyisocyanates, with the hydroxyl groups of the hydroxyl-containing poly(alkylene phosphates) present in the composition according to the invention.

The composition according to the invention is generally employed in an amount of about 0.5 to about 30 parts by weight, preferably about 3 to about 25 parts by weight, based on 100 parts by weight of polyol component.

The polyurethanes are polymers based on isocyanate and containing predominantly urethane and/or isocyanurate and/or allophanate and/or uretdione and/or urea and/or carbodiimide groups. The production of polymers based on isocyanate is known per se and described in DE-A 16 94 142 (=GB 1 211 405), DE-A 16 94 215 (=U.S. Pat. No. 3,580,890) and DE-A 17 20 768 (=U.S. Pat. No. 3,620,986) for example.

The polyurethanes according to the invention are thermosetting polyurethanes, polyurethane foams, polyurethane elastomers, thermoplastic polyurethanes, polyurethane coatings and paints, polyurethane adhesives and binders or polyurethane fibres.

In a preferred embodiment of the invention, the polyurethanes according to the invention are polyurethane foams.

Polyurethane foams are broadly divided into flexible and rigid foams. Although flexible and rigid foams may in general exhibit roughly the same density and composition, flexible polyurethane foams exhibit only a low degree of crosslinking and offer only scant resistance to deformation by compressive stress. By contrast, the structure of rigid polyurethane foams consists of highly crosslinked units and the deformation resistance of the rigid polyurethane foam under compressive stress is very high. The typical rigid polyurethane foam is closed-cell and exhibits only low thermal conductivity. Primary factors influencing the subsequent foam structure and foam properties during the production of polyurethanes via reaction of polyols with isocyanates are the structure and molar mass of the polyol, and the reactivity and number (functionality) of hydroxyl groups present in the polyol. Further details concerning rigid and flexible foams, the starting materials that can be used to produce these, and also processes for producing same, may be found in Norbert Adam, Geza Avar, Herbert Blankenheim, Wolfgang Friederichs, Manfred Giersig, Eckehard Weigand, Michael Halfmann, Friedrich-Wilhelm Wittbecker, Donald-Richard Larimer, Udo Maier, Sven Meyer-Ahrens, Karl-Ludwig Noble and Hans-Georg Wussow: "Polyurethanes", Ullmann's Encyclopedia of Industrial Chemistry Release 2005, Electronic Release, 7th ed., chap. 7 ("Foams"). Wiley-VCH, Weinheim 2005.

The polyurethane foam of the present invention preferably has an envelope density of 10-130 kg/m$^3$. It more preferably has an envelope density of 15-40 kg/m$^3$.

The isocyanate-based PU foams of the present invention are generally produced using the following starting components:

1. Organic polyisocyanate components (i) from the series of aliphatic, cycloaliphatic, araliphatic, aromatic and heterocyclic polyisocyanates (cf. for instance DE-A 27 32 292), for example those of the formula Q(NCO)$_n$, where n is from 2 to 4, preferably from 2 to 3, and Q is an aliphatic hydrocarbon radical having 2 to 18, preferably 6 to 10 C30 atoms, a cycloaliphatic hydrocarbon radical having 4 to 15, preferably 5 to 10 carbon atoms, an aromatic hydrocarbon radical having 6 to 15, preferably 6 to 13 carbon atoms or an araliphatic hydrocarbon radical having 8 to 15, preferably 8 to 13 carbon atoms. Particular preference is generally given to the industrially readily obtainable polyisocyanates derived from 2,4- and/or 2,6-tolylene diisocyanate and/or from 4,4'- and/or 2,4'-diphenylmethane diisocyanate.

2. Polyol components (ii) containing at least two isocyanate-reactive hydrogen atoms and having a molecular weight of from 400 to 8000 g/mol. This is to be understood as meaning not only amino-, thio- or carboxyl-containing compounds but preferably hydroxyl-containing compounds (polyols), in particular polyols having from 2 to 8 hydroxyl groups. If the polyurethane foam is to be a flexible foam, it is preferable to use polyols having molar masses of 2000 to 8000 g/mol and 2 to 6 hydroxyl groups per molecule. If, by contrast, a rigid foam is to be produced, it is preferable to use highly branched polyols having molar masses of 400 to 1000 g/mol and 2 to 8 hydroxyl groups per molecule. Said polyols are in particular polyethers and polyesters and also polycarbonates and polyester amides of the type known per se for the production of homogeneous and of cellular polyurethanes and as described for instance in DE-A 28 32 253 (=U.S. Pat. No. 4,263,408) and in EP 1 555 275 A2 (=U.S. Pat. No. 2,005,159 500). The polyesters and polyethers having two or more hydroxyl groups are preferable for the purposes of the present invention.

3. Optionally chain extenders and/or crosslinkers. These are compounds having two or more isocyanate-reactive hydrogen atoms and a molecular weight of from 32 to 399 g/mol. This is also to be understood as comprehending hydroxyl- and/or amino- and/or thio- and/or carboxyl-containing compounds, preferably hydroxyl- and/or amino-containing compounds. These compounds generally have from 2 to 8, preferably from 2 to 4 isocyanate-reactive hydrogen atoms. Examples thereof are likewise described in DE-A 28 32 253 (=U.S. Pat. No. 4,263,408).

4. Water and/or volatile substances such as blowing agents, for example n-pentane, i-pentane, cyclopentane, halogen-containing alkanes, such as trichloromethane, methylene chloride or chlorofluoroalkanes, gases, such as $CO_2$ and others. A mixture of two or more blowing agents may also be used.

5. It is optional to use auxiliary and additive agents, such as catalysts of the type known per se, surfactant added substances, such as emulsifiers and foam stabilizers, reaction retarders, e.g. acidic substances such as hydrochloric acid or organic acyl halides, further cell regulators of the type known per se, such as paraffins or fatty alcohols and dimethylpolysiloxanes and also pigments or dyes and further flame retardants, also stabilizers against ageing and weathering effects, scorch inhibitors, plasticizers, fungistatic and bacteriostatic substances and also fillers, such as barium sulphate, diatomaceous earth, carbon black or whiting (DE-A 27 32 292=U.S. Pat. No. 4,248, 930). As scorch inhibitors there may be present in particular sterically hindered trialkylphenols, alkyl esters of 3-(3,5-di-ten-butyl-4-hydroxyphenyl)-propionic acid, benzofuran-2-ones, secondary aromatic amines, phosphites, phenothiazines or tocopherols. Details about the use and performance of these auxiliary and additive agents may be found in Kunststoff-Handbuch, volume VII, Carl Hanser Verlag, Munich, 1993, at pages 104 to 123.

As further flame retardants, one or more compounds from the series
a) organophosphorus compounds, for example triethyl phosphate, aliphatic bisphosphates, dimethyl methanephosphonate, diethyl ethanephosphonate, dimethyl propanephosphonate, oligomeric phosphates or phosphonates, hydroxyl-containing phosphorus compounds, 5,5-dimethyl-1,3,2-dioxaphosphorinane 2-oxide derivatives, 6H-dibenz[c,e][1,2]oxaphosphorine 6-oxide derivatives, for example N$^1$,N$^2$-bis(6-oxido-6H-dibenz[c,e][1,2]oxaphosphorin-6-yl)-1,2-ethanediamine,
b) salt-type phosphorus compounds, for example ammonium phosphate, ammonium polyphosphate, melamine phosphate, melamine polyphosphate, metal melamine polyphosphates, metal salts of dialkylphosphinic acids, metal salts of alkanephosphonic acids,
c) nitrogen compounds, for example melamine and melamine cyanurate, and
d) inorganic flame retardants, for example aluminium hydroxide, boehmite, magnesium hydroxide, expandable graphite or clay minerals may optionally be included in the inventive compositions in the polyurethane foam of the present invention.

The polyurethane foams of the present invention can thus be produced as rigid or flexible foams by choosing the starting materials, in particular the polyol component (ii), in the appropriate manner easily derivable from the prior art.

The polyurethanes obtainable by the invention are preferably employed in furniture cushioning, textile inserts, mattresses, vehicle seats, armrests, components, seat and instrument panel trim, cable sheathing, seals, coatings, paints, adhesives, adhesion promoters and fibres.

The compositions according to the invention employed for producing the polyurethanes according to the invention have a low content of five-membered cyclic phosphates. Said compositions thus exhibit a low propensity for acid formation and low volatility.

The compositions according to the invention are liquid and thus amenable to metered addition. Said compositions react with the other starting materials used for producing the polyurethanes (the organic isocyanate components (i)) and are thus securely integrated in the polymer matrix. The foams produced with the hydroxyl-containing poly(alkylene phosphates) not only meet the flame retardancy requirements but also exhibit particularly low fogging values.

The examples which follow more particularly elucidate the invention without any intention to limit the invention.

EXAMPLES

The parts referred to in what follows are parts by weight.

Synthesis Example S1

Synthesis of a Poly(Alkylene Chlorophosphate) of Formula (V), where a Represents the Radical —CH$_2$CH$_2$OCH$_2$CH$_2$— (as Per Example S4 in EP 2 687 534 A1)

In a reactor fitted with a stirrer, thermometer, dropping funnel, reflux cooler and vacuum means, 118.7 parts of diethylene glycol were added dropwise to 306.7 parts of phosphorus oxychloride at 10-20° C. and 500-700 mbar. On completion of the dropwise addition, the pressure was reduced further to a final pressure of 5-15 mbar, and the temperature raised to 20-30° C. A virtually colourless liquid residue comprising 37.4 wt % of chlorine remained.

Synthesis Examples S2 to S4

Synthesis of Inventive Compositions Comprising Hydroxyl-Containing Poly(Alkylene Phosphates) of Formula (I) where the Radicals R$^1$, R$^2$, R$^3$ and R$^4$ Represent Either Ethyl or the Radical —CH$_2$—CHCH$_3$—OH or —CHCH$_3$—CH$_2$—OH, Wherein One or More of the Radicals R$^1$, R$^2$, R$^3$ and R$^4$ Represents —CH$_2$—CHCH$_3$—OH or —CHCH$_3$—CH$_2$—OH and a in Each Case Represents the Radical —CH$_2$CH$_2$OCH$_2$CH$_2$—.

In a reactor fitted with a stirrer, thermometer, dropping funnel, reflux cooler and vacuum means, the amounts of ethanol and water indicated in table 1 were admixed with stirring at 15° C. with the indicated amount of poly(alkylene chlorophosphate) from example S1. The reaction mixture was stirred for a further four hours and then freed of volatile constituents by distillation. The residue that remained was reacted at 70° C. with the indicated amount of propylene oxide. Finally, the volatile constituents were in turn removed completely by distillation. A residue of the product in the form of a colourless liquid remained. The analytical results are likewise summarized in table 1.

TABLE 1

Raw materials employed (parts by weight) for producing the synthesis examples S2 to S4 and properties of the products.

| | | Synthesis example | | |
|---|---|---|---|---|
| | Unit | S2 | S3 | S4 |
| poly(alkylene chlorophosphate) from example S1 | parts by weight | 100.7 | 203.8 | 100.1 |
| ethanol | parts by weight | 163.8 | 326.8 | 163.5 |
| water | parts by weight | 6.67 | 28.78 | 31.15 |
| water/(water + ethanol) | mol/mol · 100% | 9% | 18% | 33% |
| propylene oxide | parts by weight | 39.5 | 148.6 | 116.7 |
| acid number | mg KOH/g | 0.22 | 0.31 | 0.05 |
| hydroxyl number | mg KOH/g | 86 | 122 | 166 |
| viscosity | mPas at 23° C. | 134 | 273 | 786 |
| integral of the signals between 13 and 18 ppm in the $^{31}$P NMR Spektrum | area % | 1.7% | 2.1% | 4.1% |

Synthesis Example S5 to S7

Synthesis of Hydroxyl-Containing Poly(Alkylene Phosphates) Based on Phosphorus Pentoxide as Per EP 0 771 810 A1 (Non-Inventive)

A reactor fitted with a stirrer, thermometer, powder funnel, reflux cooler and vacuum means was initially charged with the amount of ethanol indicated in table 2. The indicated amount of phosphorus pentoxide was added portionwise such that the temperature did not exceed 40° C. Once addition was complete the mixture was heated to 80° C. and held at this temperature for six hours. The mixture was then cooled to 60° C. and the powder funnel was exchanged for a dropping funnel from which the indicated amount of propylene oxide was added dropwise. The reaction temperature was gradually increased from 60° C. to 100° C. over the course of this addition. Once the dropwise addition was complete the mixture was held at 100° C. for one hour. Finally, the volatile constituents were removed completely by distillation. A brown, liquid residue remained.

TABLE 2

Raw materials employed (parts by weight) for producing the noninventive synthesis examples S5 to S7 and properties of the products.

| | Unit | S5 | S6 | S7 |
|---|---|---|---|---|
| phosphorus pentoxide | parts by weight | 283.9 | 42.58 | 42.58 |
| ethanol | parts by weight | 184.3 | 27.64 | 23.04 |
| propylene oxide | parts by weight | 645.0 | 112.6 | 132.2 |
| acid number | mg KOH/g | 0.16 | 4.75 | 0.24 |
| hydroxyl number | mg KOH/g | 165 | 155 | 77 |
| integral of the signals between 13 and 18 ppm in the $^{31}$P NMR Spektrum | area % | 16.4% | 22.2% | 35.1% |

Production of Flexible Polyurethane Foams

TABLE 3

Raw materials employed for producing inventive flexible polyurethane foams (examples B1 to B3) and noninventive flexible polyurethane foams (comparative examples V1 to V4)

| Component | Function | Description |
|---|---|---|
| A | polyol | Arcol ® 1105 (Bayer MaterialScience), polyether polyol with OHN 56 mg KOH/g |
| B | blowing agent | water |
| C | catalyst | Addocat 108 ® (Rhein Chemie), 70% solution of bis(2-dimethylaminoethyl) ether in dipropylene glycol |
| D | catalyst | Addocat ® SO (Rhein Chemie), tin(II) 2-ethylhexanoate |
| E | stabilizer | Tegostab ® B 8232 (Degussa), silicone stabilizer |
| F1 | flame retardant | tris(2,3-dichloroisopropyl) phosphate, TDCP |
| F2 | flame retardant | Disflamoll ® DPK (LANXESS Deutschland GmbH), diphenyl cresyl phosphate |
| F3 | flame retardant | product from synthesis example S5 (noninventive) |
| F4 | flame retardant | product from synthesis example S2 (inventive) |
| F5 | flame retardant | product from synthesis example S3 (inventive) |
| F6 | flame retardant | product from synthesis example S4 (inventive) |
| G | diisocyanate | Desmodur ® T 80 (Bayer MaterialScience), tolylene diisocyanate, isomer mixture |

Production of Flexible Polyurethane Foams

The raw materials for producing flexible polyurethane foams are specified in table 3. The components specified in table 4 in terms of type and amount with the exception of the diisocyanate (component G) were stirred to afford a homogeneous mixture. The diisocyanate (component G) was then added and briefly stirred in vigorously. This increased the amount of diisocyanate as a function of the hydroxyl number of the flame retardant such that an equal index (ratio of amount of isocyanate to hydroxyl groups) of 108 was maintained in all formulations. After a cream time of 15-20 s and a full-rise time of 140-180 s a flexible polyurethane foam having an envelope density of 33 kg/m$^3$ was obtained. All experiments afforded uniformly fine-celled foams.

Determination of Flame Retardancy

The flexible polyurethane foams were tested in accordance with the specifications of Federal Motor Vehicle Safety Standards FMVSS-302 and classified according to the flammability ratings SE (self-extinguishing), SE/NBR (self-extinguishing/no burn rate), SE/BR (self-extinguishing/with burn rate), BR (burn rate) and RB (rapid burn). The flammability tests were carried out five times for each example. The poorest result for each series of five is shown in table 4.

Fogging Determination

The fogging behaviour of the flexible polyurethane foams was analyzed as per DIN 75201 B. The measured condensate amounts after storage for 16 hours at 100° C. are shown in table 4.

TABLE 4

Flexible polyurethane foam composition (parts by weight) and test results for inventive examples B1 to B3 and noninventive comparative examples V1 to V4

| Example | V1 | V2 | C3 | C4 | B1 | B2 | B3 |
|---|---|---|---|---|---|---|---|
| A | 100 | 100 | 100 | 100 | 100 | 100 | 100 |
| B | 3.0 | 3.0 | 3.0 | 3.0 | 3.0 | 3.0 | 3.0 |
| C | 0.08 | 0.08 | 0.08 | 0.08 | 0.08 | 0.08 | 0.08 |
| D | 0.16 | 0.16 | 0.16 | 0.16 | 0.16 | 0.16 | 0.16 |
| E | 0.80 | 0.80 | 0.80 | 0.80 | 0.80 | 0.80 | 0.80 |
| F1 | | 6 | | | | | |
| F2 | | | 6 | | | | |
| F3 | | | | 6 | | | |
| F4 | | | | | 6 | | |
| F5 | | | | | | 6 | |
| F6 | | | | | | | 6 |
| G | 40.9 | 40.9 | 40.9 | 42.6 | 41.8 | 42.1 | 42.6 |
| MVSS rating | RB | SE | BR | SE | SE | SE | SE |
| fogging condensate [mg] as per DIN 75201 B | 0.12 | 0.79 | 0.72 | 1.74 | 0.36 | 0.27 | 0.25 |

Evaluation of Flexible Polyurethane Foam Test Results

In the absence of a flame retardant (comparative example V1) the flexible polyurethane foam burns rapidly (MVSS flammability rating RB) but exhibits a very low fogging value. A foam comprising tris(dichloroisopropyl) phosphate (comparative example V2) exhibits a substantial flame retardant additive fogging contribution and achieves the best MVSS flammability rating SE (self-extinguishing) in all repetitions of the flammability test. However, tris(dichloroisopropyl) phosphate brings with it the abovedescribed disadvantages of a halogen-containing flame retardant. While the use of the halogen-free flame retardant diphenyl cresyl phosphate (comparative example V3) circumvents this problem and also achieves a low fogging value, the flame retardancy, of MVSS flammability rating BR, is insufficient. The flame retardant employed in comparative example V4 has a very good flame retardancy (MVSS flammability rating SE, i.e. self-extinguishing) but exhibits relatively high fogging values attributable to cyclic phosphates.

The examples B1 to B3 show that the flexible polyurethane foams according to the invention achieve the best flammability rating SE (self-extinguishing) in all repetitions of the flammability test and also have the lowest fogging values.

What is claimed is:

1. A hydroxyl-containing poly(alkylene phosphate) composition having a reduced residual content of undesired phosphorous-containing byproducts, the composition comprising at least one hydroxyl-containing poly(alkylene phosphate) of formula (I)

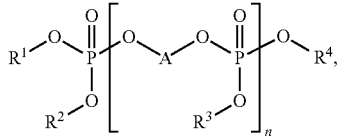

where
n is an integer from 1 to 100,
$R^1$, $R^2$, $R^3$ and $R^4$ independently of one another represent a $C_1$- to $C_8$-alkyl radical, or a radical of formula —$(CHR^5—CHR^6—O)_m$—H,
where
m is an integer from 1 to 5, and
$R^5$ and $R^6$, independently of one another, represent hydrogen or methyl,
with the proviso that one or more of the radicals $R^1$, $R^2$, $R^3$ and $R^4$, but not simultaneously all of the radicals $R^1$, $R^2$, $R^3$ and $R^4$, represent a radical of formula —$(CHR^5—CHR^6—O)_m$—H, and
A represents a straight-chain or branched $C_4$- to $C_{20}$-alkylene radical, or a $C_3$- to $C_6$-cycloalkylene radical, or a radical of formula —$CH_2—CH=CH—CH_2$—, a radical of formula —$CH_2—C≡C—CH_2$—, a radical of formula —$CHR^5—CHR^6—(O—CHR^7—CHR^8)_a$—, a radical of formula —$CHR^5—CHR^6—S(O)_b—CHR^7—CHR^8$—, or a radical of formula —$(CHR^5—CHR^6—O)_c—R^9—(O—CHR^7—CHR^8)_d$—,
where
a is an integer from 0 to 5,
b is an integer from 0 to 2,
c and d are independently of one another an integer of 1 to 5, $R^5$, $R^6$, $R^7$ and $R^8$, independently of one another, represent hydrogen or methyl,
$R^9$ represents the radical —$CH_2—CH=CH—CH_2$—, the radical —$CH_2—C≡C—CH_2$—, a 1,2-phenylene radical, a 1,3-phenylene radical, a 1,4-phenylene radical, or a radical of formula (II)

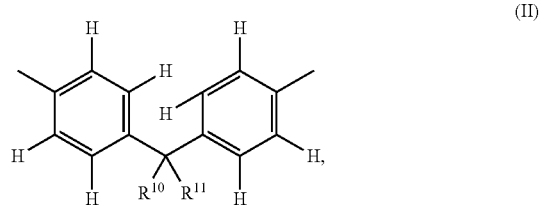

or a radical of formula (III)

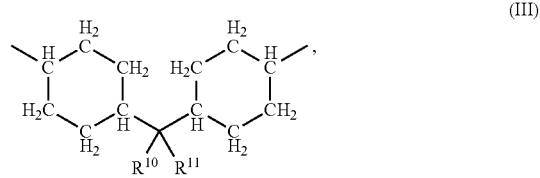

or a radical of formula (IV)

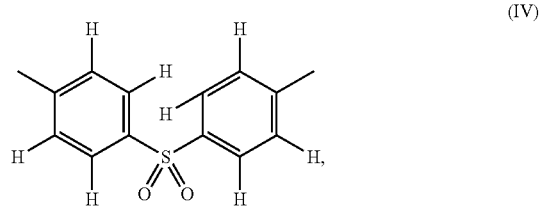

or a radical of formula
—C(=O)—$R^{12}$—C(=O)—,
wherein
$R^{10}$ and $R^{11}$ each, independently of one another, represent hydrogen or $C_1$- to $C_4$-alkyl,
or
$R^{10}$ and $R^{11}$ together with the carbon atom to which they are bonded represent an optionally alkyl-substituted carbocyclic ring having 4 to 8 carbon atoms,
and
$R^{12}$ represents a straight-chain or branched $C_2$- to $C_8$-alkylene radical, a $C_3$- to $C_6$-cycloalkylene radical, a 1,2-phenylene radical, a 1,3-phenylene radical, or a 1,4-phenylene radical,
wherein, in a $^{31}$P NMR spectrum of the composition in $CDCl_3$ as solvent, with 85 wt % phosphoric acid as external standard, undesired phosphorous-containing byproducts produce resonance signals from 13 to 18 ppm, and, for the composition, an area under all resonance signals from 13 to 18 ppm is about 5 percent or less of the total area of all resonance signals from −30 to 200 ppm.

2. The composition according to claim 1, wherein, in the at least one hydroxyl-containing poly(alkylene phosphate) of formula (I), n is an integer from 1 to 10,
$R^1$, $R^2$, $R^3$ and $R^4$ independently of one another represent ethyl, n-propyl, isopropyl, n-butyl or isobutyl or a radical of formula —(CHR$^5$—CHR$^6$—O)$_m$—H, where
  m is an integer from 1 to 2, and
  $R^5$ and $R^6$, independently of one another, represent hydrogen or methyl,
with the proviso that one or more of the radicals $R^1$, $R^2$, $R^3$ and $R^4$, but not simultaneously all of the radicals $R^1$, $R^2$, $R^3$ and $R^4$, represent a radical of formula —(CHR$^5$—CHR$^6$—O)$_m$—H, and
A represents a straight-chain $C_4$- to $C_6$-alkylene radical or a radical of formula —CHR$^5$—CHR$^6$—(O—CHR$^7$—CHR$^8$)$_a$—, where
  a is an integer from 0 to 2, and
  $R^5$, $R^6$, $R^7$ and $R^8$, independently of one another, represent hydrogen or methyl.

3. The composition according to claim 1, wherein, in the at least one hydroxy-containing poly(alkylene phosphate) of formula (I),
n is an integer from 1 to 10,
$R^1$, $R^2$, $R^3$ and $R^4$ independently of one another represent ethyl, n-propy or n-butyl or a radical of formula —(CHR$^5$—CHR$^6$—O)$_m$—H, where
  m is 1 or 2, and
  $R^5$ and $R^6$, independently of one another, represent hydrogen or methyl,
with the proviso that one or more of the radicals $R^1$, $R^2$, $R^3$ and $R^4$, but not simultaneously all of the radicals $R^1$, $R^2$, $R^3$ and $R^4$, represent a radical of formula —(CHR$^5$—CHR$^6$—O)$_m$—H, and
A represents a straight-chain $C_4$-alkylene radical or a radical of formula —CHR$^5$—CHR$^6$—(O—CHR$^7$—CHR$^8$)$_a$—, where
  a is 0 or 1,
  $R^5$ and $R^6$, independently of one another, represent hydrogen or methyl, and
  $R^7$ and $R^8$ are identical and represent hydrogen.

4. The composition according to claim 1, wherein, in the at least one hydroxy-containing poly(alkylene phosphate) of formula (I),
n is an integer from 1 to 10,
$R^1$, $R^2$, $R^3$ and $R^4$, independently of one another, represent ethyl, or the radical —CH$_2$—CHCH$_3$—OH, or the radical —CHCH$_3$—CH$_2$—OH, wherein one or more of the radicals $R^1$, $R^2$, $R^3$ and $R^4$, but not simultaneously all of the radicals $R^1$, $R^2$, $R^3$ and $R^4$, represent —CH$_2$—CHCH$_3$—OH or —CHCH$_3$—CH$_2$—OH,
A represents the radical —CH$_2$CH$_2$OCH$_2$CH$_2$—;
the total area under all resonance signals from −30 to 200 ppm relates to the sum of all phosphorus atoms present in the composition, wherein the area under all resonance signals from 13 to 18 ppm in relation to the total area under all resonance signals from −30 to 200 ppm, corresponds to mol % of the undesired phosphorous-containing byproducts, and the composition contains about 5 mol percent or less of the undesired phosphorous-containing byproducts; and the undesired phosphorous-containing byproducts that produce the resonance signals from 13 to 18 ppm comprise cyclic five-membered phosphoric esters having at least one structural unit of formula

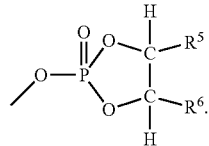

5. The composition according to claim 1, having a hydroxyl number of 15 to 300 mg KOH/g.

6. The composition according to claim 1, having a viscosity at 23° C. of 10 mPas to 10,000 mPas.

7. The composition according to claim 1, wherein the composition is a flame retardant for synthetic polymers, modified or unmodified natural polymers, wood-based materials, leather or paper.

8. A flame retardant preparation comprising the composition according to claim 1 and at least one auxiliary/added substance.

9. A process for producing a flame retardant polyurethane comprising the composition according to claim 1, the process comprising reacting at least one organic polyisocyanate with at least one polyol component containing at least two isocyanate-reactive hydrogen atoms with customary blowing agents, stabilizers, activators and/or further customary auxiliary/added substances in the presence of the composition according to claim 1.

10. The composition according to claim 1, wherein the total area under all resonance signals from −30 to 200 ppm relates to the sum of all phosphorus atoms present in the composition, and the area under all resonance signals from 13 to 18 ppm in relation to the total area under all resonance signals from −30 to 200 ppm, corresponds to mol % of undesired phosphorous-containing byproducts and the composition contains about 5 percent or less of the undesired phosphorous-containing byproducts.

11. The composition according to claim 1, wherein the undesired phosphorous-containing byproducts that produce resonance signals from 13 to 18 ppm comprise cyclic five-membered phosphoric esters having at least one structural unit of formula

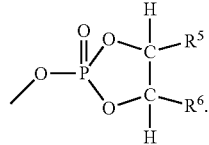

12. The composition according to claim 1, wherein:
the area under all resonance signals from 13 to 18 ppm is about 3 percent or less of the total area of all resonance signals from −30 to 200 ppm; and
the composition contains about 3 mol percent or less of the undesired phosphorous-containing byproducts.

* * * * *